(12) United States Patent
Daisaku (10) Patent No.: US 10,264,876 B2
(45) Date of Patent: Apr. 23, 2019

(54) ORAL CLEANING DEVICE

(71) Applicant: DAISAKU SHOJI LTD., Tokyo (JP)

(72) Inventor: Ippei Daisaku, Tokyo (JP)

(73) Assignee: DAISAKU SHOJI LTD., Tokyo (JP)

( * ) Notice: Subject to any disclaimer, the term of this patent is extended or adjusted under 35 U.S.C. 154(b) by 0 days.

(21) Appl. No.: 15/553,537

(22) PCT Filed: Feb. 27, 2015

(86) PCT No.: PCT/JP2015/001036
§ 371 (c)(1),
(2) Date: Dec. 11, 2017

(87) PCT Pub. No.: WO2016/135780
PCT Pub. Date: Sep. 1, 2016

(65) Prior Publication Data
US 2018/0103750 A1 Apr. 19, 2018

(51) Int. Cl.
*A61C 17/22* (2006.01)
*A61C 17/34* (2006.01)
(Continued)

(52) U.S. Cl.
CPC ............ *A46B 13/023* (2013.01); *A61B 17/24* (2013.01); *A61C 17/221* (2013.01); *A61C 17/222* (2013.01); *A61C 17/3481* (2013.01); *A46B 5/0095* (2013.01); *A46B 2200/108* (2013.01); *A61B 17/244* (2013.01); *A61C 15/00* (2013.01)

(58) Field of Classification Search
CPC ................. A46B 13/02; A61C 17/34
See application file for complete search history.

(56) References Cited

U.S. PATENT DOCUMENTS 5,150,492 A * 9/1992 Suroff .................... A61C 17/20
15/22.1
5,504,959 A * 4/1996 Yukawa ............. A61C 17/3472
15/22.1
6,920,659 B2 * 7/2005 Cacka .................. A61C 17/225
15/22.1
(Continued)

FOREIGN PATENT DOCUMENTS

JP        2-174804 A       7/1990
JP        H04-112629       9/1992
(Continued)

OTHER PUBLICATIONS

International Search Report for PCT/JP2015/001036, dated May 26, 2015, and its English translation provided by WIPO.
(Continued)

*Primary Examiner* — Michael Jennings
(74) *Attorney, Agent, or Firm* — Ladas & Parry, LLP (57) ABSTRACT

An oral cleaning device, which can vibrate an oral cleaning tool such as a tooth brush, a tongue brush or an interdental brush, is provided.
An oral cleaning device has a supporting part (20) which supports an oral cleaning tool; a clamping fixing part (5) which is movable close to or away from the supporting part (5) and which fixes the oral cleaning tool (100) to the supporting part (20) when being moved close to the supporting part (20); and a vibrating part (30) and (31) which vibrates the oral cleaning tool (10) fixed to the supporting part (20) by vibrating the supporting part (20) or the clamping fixing part (5).

10 Claims, 8 Drawing Sheets

(51) Int. Cl.
*A46B 13/02* (2006.01)
*A61B 17/24* (2006.01)
*A61C 15/00* (2006.01)
*A46B 5/00* (2006.01)

(56) References Cited

U.S. PATENT DOCUMENTS

| | | | |
|---|---|---|---|
| 8,336,155 B2* | 12/2012 | Crossman | A61C 17/3463 |
| | | | 15/167.1 |
| 8,943,634 B2* | 2/2015 | Sokol | A61C 17/3481 |
| | | | 15/22.1 |
| 9,265,338 B1* | 2/2016 | Cygler | A61C 17/222 |
| 2006/0090274 A1 | 5/2006 | Kim | |
| 2012/0266397 A1* | 10/2012 | Iwahori | A46B 15/0006 |
| | | | 15/22.1 |
| 2013/0061412 A1* | 3/2013 | Vashi | A46B 5/0095 |
| | | | 15/106 |

FOREIGN PATENT DOCUMENTS

| | | |
|---|---|---|
| JP | H05-001320 | 1/1993 |
| JP | 05-091922 A | 4/1993 |
| JP | 10-216159 A | 8/1998 |
| JP | 2006-122669 A | 5/2006 |
| JP | 2011-139844 A | 7/2011 |

OTHER PUBLICATIONS

Written Opinion of the International Search Authority for PCT/JP2015/001036, dated May 26, 2015, and its English translation provided by Bing.com Microsoft Translator.

* cited by examiner

ORAL CLEANING DEVICE

CROSS-REFERENCE TO RELATED APPLICATION

The present application is the U.S. national phase of PCT Application No. PCT/JP2015/001036 filed on Feb. 27, 2015, and entitled "ORAL CLEANING DEVICE", the disclosure of which is incorporated herein by reference in its entirety.

TECHNICAL FIELD

The present invention relates to an oral cleaning device for cleaning in a mouth such as a tooth brush, a tongue brush or an interdental brush.

BACKGROUND ART

Conventionally, electric tooth brushes which vibrate their tooth brush parts for brushing teeth have been known (e.g., refer to Patent Literature 1). It can be expected that teeth can be brushed more cleanly by such an electric tooth brush than by hand. A tooth brush part of such an electric tooth brush is consumable, and thus is necessary to be replaced after being used at a certain extent.

CITATION LIST

Patent Literature

Patent Literature 1: JP 2011-139844 A

SUMMARY OF INVENTION

Technical Problem

However, there is no other way than to use a manufacturer's designated part as this tooth brush part, and it is difficult for a user to choose it freely. In addition, such tooth brush parts are usually expensive, and can be hardly obtained at low costs.

Further, in electric tooth brushes, it has been tried to vibrate such tooth brush parts, but there has been no conception of vibrating oral cleaning tools other than tooth brushes, such as tongue brushes or interdental brushes.

The present invention has been made in the light of these points, and provides an oral cleaning device that can vibrate an oral cleaning tool such as a tooth brush, a tongue brush or an interdental brush.

Solution to Problem

An oral cleaning device according to the present invention comprises:
a supporting part which supports an oral cleaning tool;
a clamping fixing part which is movable close to or away from the supporting part and which fixes the oral cleaning tool to the supporting part when being moved close to the supporting part; and
a vibrating part which vibrates the oral cleaning tool fixed to the supporting part by vibrating the supporting part or the clamping fixing part.

The oral cleaning device according to the present invention may further comprise an auxiliary fixing part which fixes the oral cleaning tool to the supporting part at a lower position, wherein the clamping fixing part may fix the oral cleaning tool to the supporting part at an upper position compared with the auxiliary fixing part.

In the oral cleaning device according to the present invention,
the auxiliary fixing part may fix a lower end of the oral cleaning tool to the supporting part.

In the oral cleaning device according to the present invention, the supporting part may be included in a main body the oral cleaning device may further comprise a rotating part which is provided on a side surface of the main body,
wherein the clamping fixing part may have a pressing part, which comes close to the supporting part and which presses the oral cleaning tool to the supporting part when the rotating part is rotated.

In the oral clearing according to the present invention,
the rotating part may have a first sealing part which shuts off a flow of liquid from the main body into the rotating part.

In the oral cleaning device according to the present invention,
the first sealing part may nave a watertight ring, and
the watertight ring may be fitted into a depressed part which is provided on a side surface of the main body.

In the oral cleaning device according to the present invention,
the rotating part may have a second sealing part which shuts off a flow of liquid from an opposite side of the supporting part into the rotating part.

In the oral cleaning device according to the present invention,
the rotating part may have a rotating main body, which is rotatable, and stick-on seal, which is stuck on a front surface of the rotating main body, and
the stick-on seal may be included in the second sealing part.

The oral cleaning device according to the present invention may further comprise a casing which covers the oral cleaning tool fixed by the clamping fixing part in a height region from a lower position of the supporting part to an upper position of the supporting part.

In the oral cleaning device according to the present invention,
the supporting part may be included in a main body,
the casing may be detachable to the main body.

In the oral cleaning device according to the present invention,
the oral cleaning tool may be a tooth brush, a tongue brush or an interdental brush.

According to the present invention, the oral cleaning tool can be fixed to the supporting part by moving the clamping fixing part close to the supporting part, and the supporting part or the clamping fixing part is vibrated in this state, whereby the oral cleaning tool fixed to the supporting part can be vibrated. Thus, only by attaching the oral cleaning tool such as a tooth brush, tongue brush or interdental brush to the oral cleaning device, the oral cleaning tool can be vibrated and exert a high cleaning function.

As an example of such a tooth brush, a favorite tooth brush of the user can work as a so-called electric toothbrush. Further, in some cases, by using a cheap tooth brush, a cleaning effect similar to that of an electric tooth brush can be obtained at a low running cost.

BRIEF DESCRIPTION OF DRAWINGS

FIG. 1(*a*) is a perspective view illustrating a decomposed oral cleaning device according to an embodiment of the present invention, and FIG. 1(b) is a perspective view illustrating the oral cleaning device according to the present invention after being composed.

DESCRIPTION OF EMBODIMENTS

<<Structure>>

Hereinafter, an embodiment of the oral cleaning device according to the present invention will be described with reference to the drawings. Herein, FIGS. 1 to 8 are views for explaining the embodiment of the present invention.

As shown in FIG. 1(b), the oral cleaning device of the embodiment has a supporting part 20 which supports an oral cleaning tool 100 such as a tooth brush, a tongue brush or an interdental brush. The oral cleaning device has a clamping fixing part 5 which is movable close to or away from the supporting part 20. The clamping fixing part 5 (specifically, a pressing part 10 described below) can fix the oral cleaning tool 100 to the supporting part 20 when being moved close to the supporting part 20.

The supporting part 20 of the present embodiment is extended in a vertical direction. The supporting part 20 is included in a main body 1, and is constituted by a part of the main body 1 close to a below-described casing 13.

Figure 4:
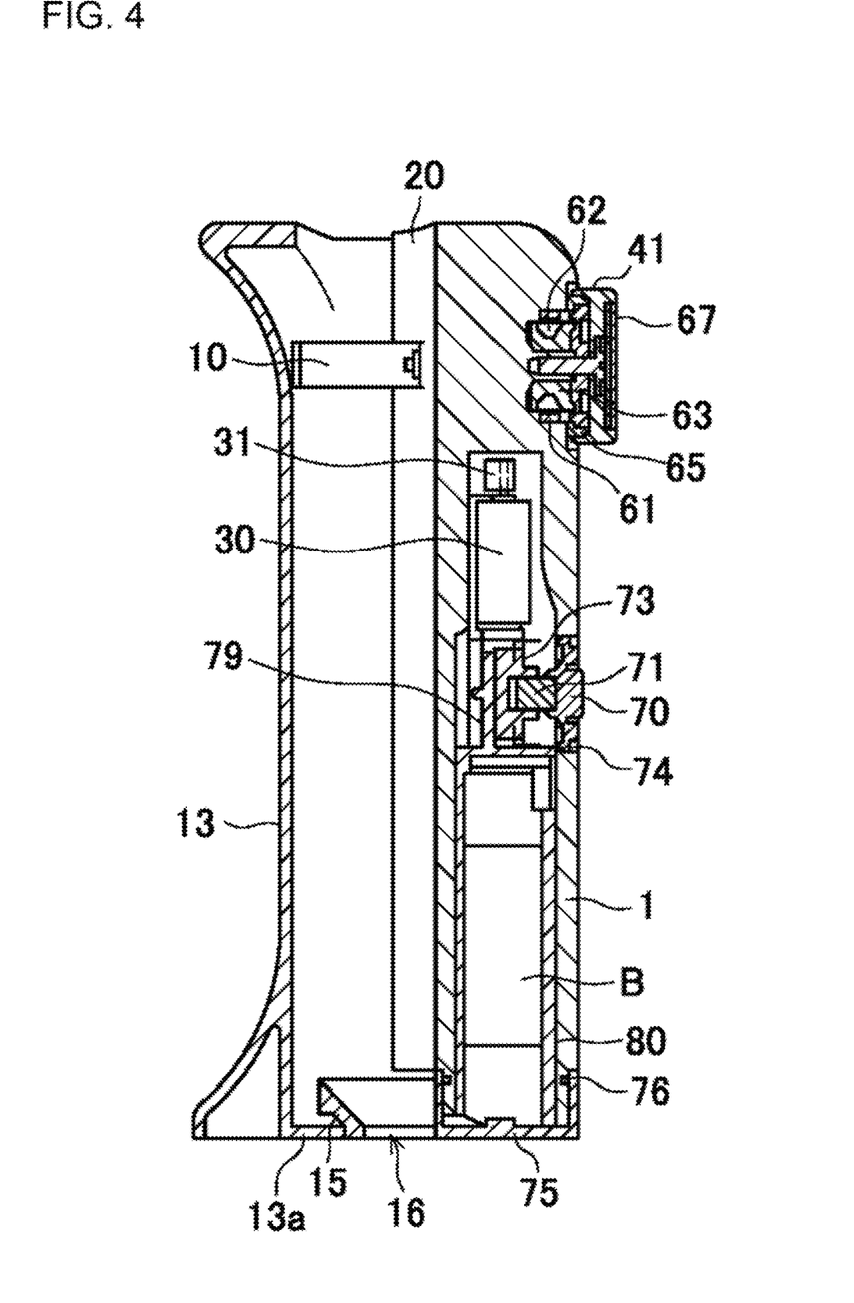
FIG. 4 is a lateral cross-sectional view of the oral cleaning device according to the embodiment of the present invention.

The oral cleaning device has vibrating parts 30 and 31 that vibrate the supporting part 20 or the clamping fixing part 5 so as to vibrate the oral cleaning tool 100 which is fixed to the supporting part 20. The vibrating parts 30 and 31 of the present embodiment include a driving part 30 such as a motor provided in the main body 1 and a balance weight 31 which is provided eccentrically at a tip of the driving part 30 also in the main body 1, as shown in FIG. 4. Then, the driving part 30 rotates the balance weight 31 so as to vibrate the main body 1, thereby consequently vibrating the oral cleaning tool 100 fixed to the supporting part 20. Incidentally, this aspect is just an example, and it is also possible to adopt a structure in which the clamping fixing part 5 is provided with the vibrating part, whereby the oral cleaning tool 100 fixed to the supporting part 20 is vibrated due to the vibration of the clamping fixing part 5. In the present embodiment, the supporting part 20 and the clamping fixing part 5 are vibrated by the vibrating parts 30 and 31.

As shown in FIGS. 3(b) and 4, the oral cleaning device has an auxiliary fixing part 15 which fixes the oral cleaning tool 100 to the supporting part 20 at a lower position. This auxiliary fixing part 15 fixes a lower end of the oral cleaning tool 100 to the supporting part 20. The auxiliary fixing part 15 is included in a lower attaching part 16 which is to be attached to a lower end of the supporting part 20 (see FIG. 1(a)). This lower attaching part 16 is detachable to the main body 1. A height position (a position in a vertical direction) of the auxiliary fixing part 15 is not necessarily near a lower end of the casing 13, and may be higher (for example, at a distance of 30% or less of a total length of the casing 13 from the lower end of the casing 13). Also, the height position of the auxiliary fixing part 15 may be adjustable. By adjusting the height position of the auxiliary fixing part 15 as described above, a lower end or a lower part of such an oral cleaning tools 100 having any length can be fixed to the supporting part 20 by the auxiliary fixing part 15.

Figure 1:
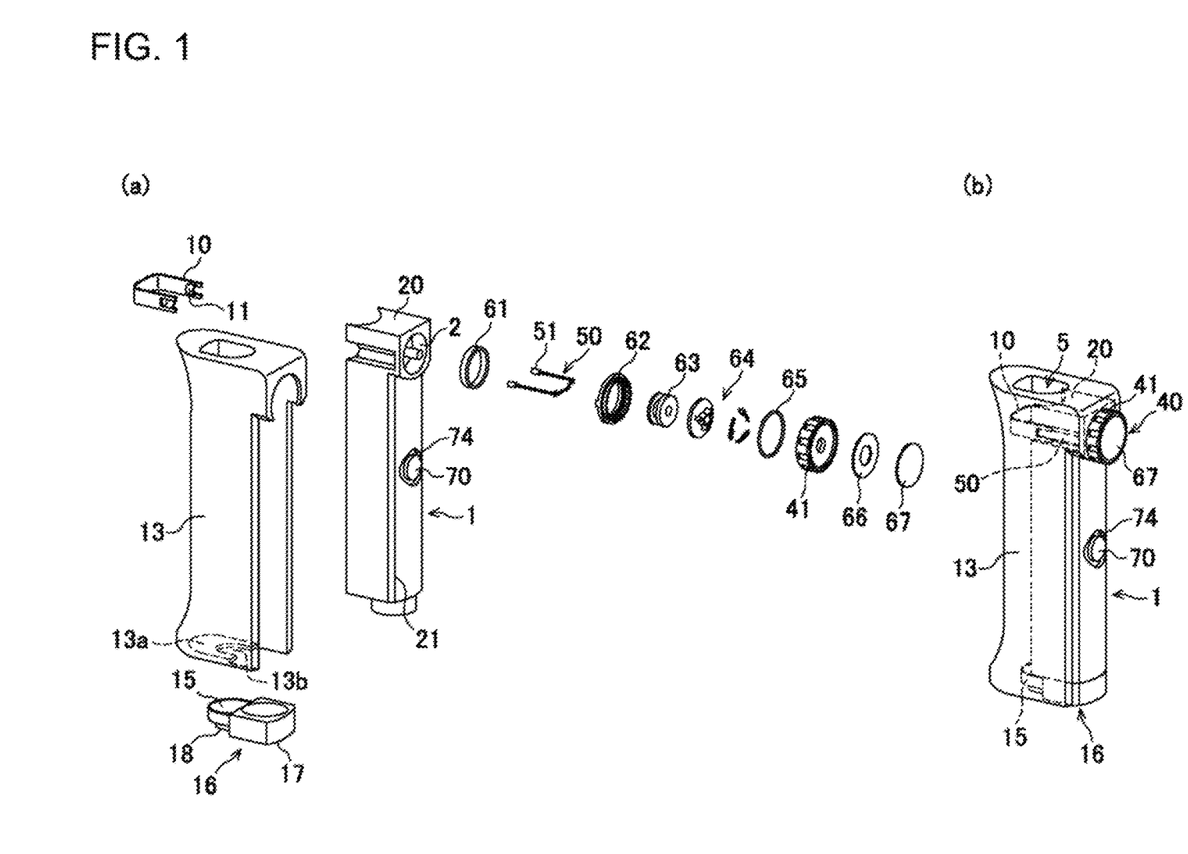

The above-described clamping fixing part 5 fixes the oral cleaning tool 100 to the supporting part 20 at a position higher than the auxiliary fixing part 15. As shown in FIG. 1(b), a rotating part 40 is provided on a side surface of the supporting part 20. The clamping fixing part 5 has: the pressing part 10 which comes close to the supporting part 20 by rotating the rotating part 40 and presses the oral cleaning tool 100 to the supporting part 20; and a connecting mechanism which is connected with the pressing part 10 and the rotating part 40 and is composed of a wire 50 and the like (see FIG. 1(a)). By rotating this connecting mechanism by the rotating part 40, the pressing part 10 is moved close to or away from the supporting part 20 (see FIGS. 7(a) and 7(b)). In the aspect shown in FIG. 1, the connecting mechanism is composed of the wire 50. This wire 50 is substantially U-shaped when it is seen from above, and is provided with a wire stopper 51 at its tip. Further, the pressing part 10 is provided with an inserting part 11, in which this wire stopper 51 is to be inserted.

Figure 2:
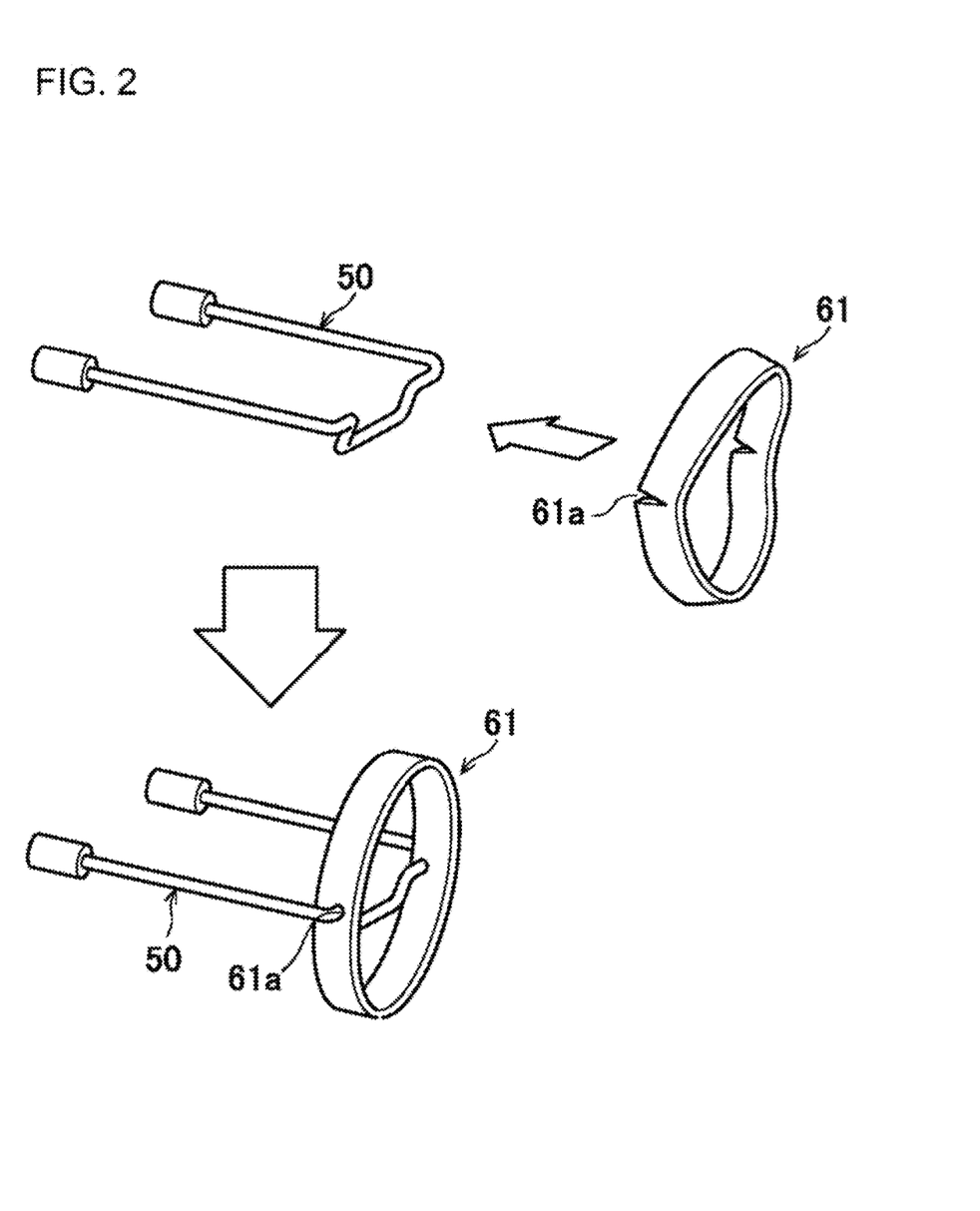
FIG. 2 is a perspective view for explaining a relation between a first sealing part and a wire according to the embodiment of the present invention.

Between the rotating part 40 and the supporting part 20, a first sealing part 61 which shuts off a flow of liquid from the supporting part 20 into the rotating part 40 is provided. In the present embodiment, this first sealing part 61 is composed of a watertight ring, and is fitted into a depressed part 2 which is provided on the main body 1. On an inner peripheral side of the first sealing part 61, a below-described reel 63 and the like are to be disposed. As shown in FIG. 2, the watertight ring that composes the first sealing part 61 is provided with a pair of cuts 61a, and the wire 50 is to be inserted into these cuts 61a.

Figure 5:
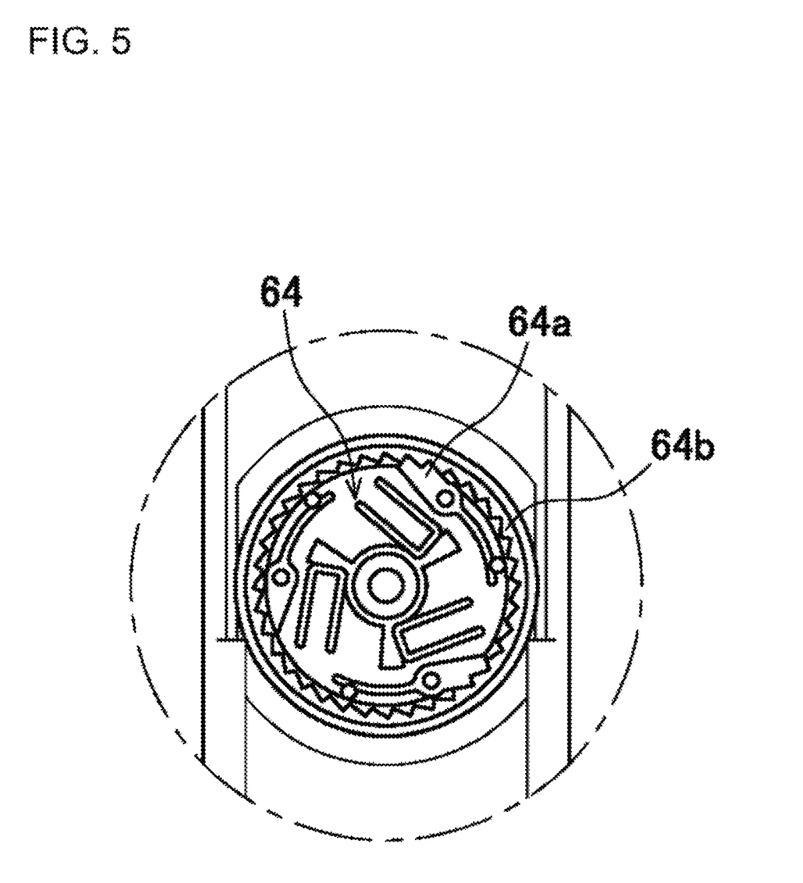
FIG. 5 is a rear view of the oral cleaning device according to the embodiment of the present invention, in which a vicinity of a button is enlarged.

In the present embodiment, the rotating part 40 has: the above-described first sealing part 61; ratchet internal teeth 62; the reel 63 which is to be provided on an inner peripheral side of the ratchet internal teeth 62; a driving disc 64 which is to be provided on a front side of the reel 63 (on a rear side of the main body 1); an O ring 65 which is to be provided on an outer peripheral side of the driving disc 64; a dial 41 which is a rotation main body having a groove for storing the O ring 65 on its inner peripheral side; a waterproof double-sided seal 66 having a torus shape, which is to be attached to a front surface of the dial 41 (a surface on a right side in FIG. 4: a rear surface of the main body 1); and a waterproof seal 67 which is to be attached onto an upside of the waterproof double-sided seal 66. Among them, the O ring 65, the waterproof double-sided seal 66 and the waterproof seal 67 compose a second sealing part 65 to 67 which shuts off a flow of liquid from an opposite side (a right side in FIG. 4) of the supporting part 20 into the rotating part 40. This structure is just an example, and the second sealing part may include only the O ring 65, the waterproof double-sided seal 66 or the waterproof seal 67. In addition, the waterproof double-sided seal 66 and the waterproof seal 67 are included in a stick-on seal. As shown in FIG. 5, the driving disc 64 has ratchet pawls 64*a* and ratchet external teeth 64*b* which are engaged with the ratchet internal teeth 62.

Figure 7:
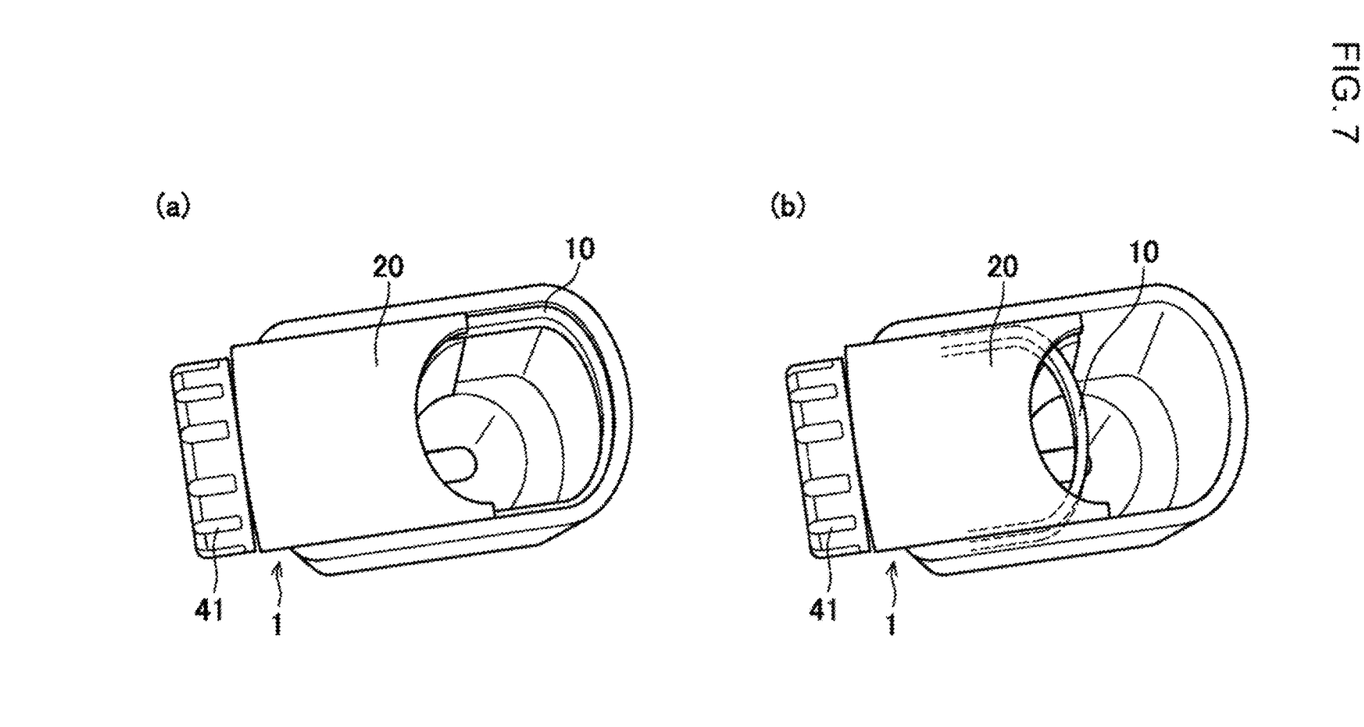
FIG. 7(a) is a plan view illustrating a state where a pressing part is away from a supporting part in the oral cleaning device according to the embodiment of the present invention.
FIG. 7(b) is a plan view illustrating a state where the pressing part is close to the supporting part.

When the dial 41 is rotated, for example, clockwise, the driving disc 64 is rotated, so that the reel 63 is also rotated so as to wind the wire 50. Then, the wire 50 is wound by the reel 63 as described above, the pressing part 10 comes close to the supporting part 20 (see FIG. 7(*a*)). Adversely, when the dial 41 is rotated, for example, counterclockwise, the wire 50 wound by the reel 63 comes into a released state (a loosened state), so that the pressing part 10 comes away from the supporting part 20 (see FIG. 7(*b*)).

As shown in FIGS. 1(*b*), 3(*b*) and 4, the casing 13 which covers the oral cleaning tool 100 fixed by the clamping fixing part 5 in a height region from a lower position of the supporting part 20 to an upper position of the supporting part 20 is provided. In the present embodiment, this casing 13 is extended from the lower end of the supporting part 20 to an upper end of the supporting part 20.

The casing 13 of the present embodiment is detachable to the main body 1 (see FIG. 1(*a*)). More specifically, a groove part 21 for guiding the casing 13 is provided on the side surface of the supporting part 20, and the casing 13 is guided by this groove part 21 so as to be attached to the supporting part 20. The casing 13 has a lower surface 13*a*, and this lower surface 13*a* is provided with a notch 13*b* in which a projecting part 18 provided at a lower end part of the lower attaching part 16 is to be inserted. In addition, the lower attaching part 16 is also provided with a groove part 17 for guiding the casing 13.

Figure 6:
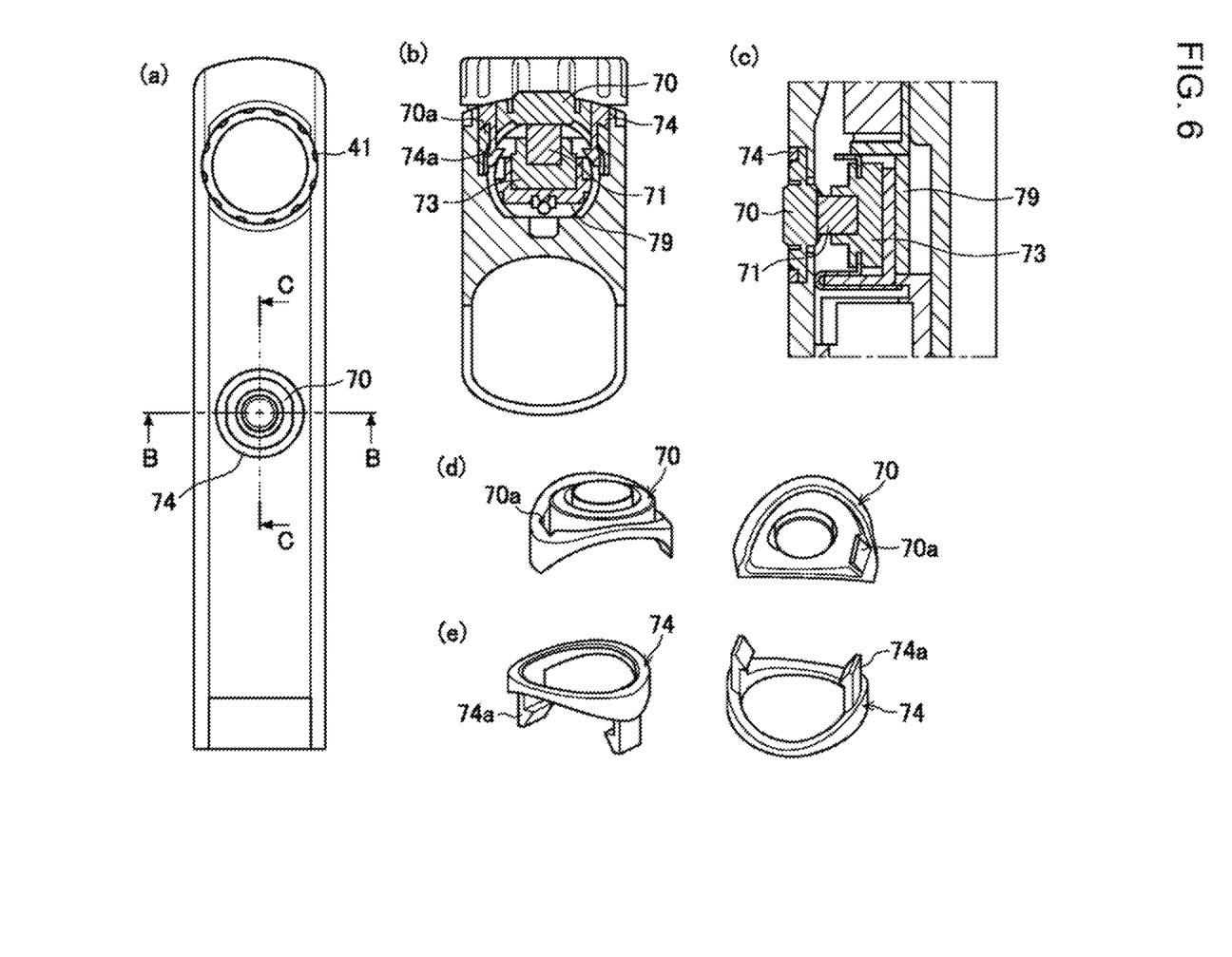
FIG. 6(a) is a rear view of the oral cleaning device according to the embodiment of the present invention.
FIG. 6(b) is a cross-sectional view taken along a line B-B in FIG. 6(a)
FIG. 6(c) is a cross-sectional view taken along a line C-C in FIG. 6(a)
FIG. 6(d) is a view enlargingly illustrating the button used in the embodiment of the preset invention.
FIG. 6(e) is a view enlargingly illustrating a button frame used in the embodiment of the preset invention.

As shown in FIG. 6, a button 70 for switching ON and OFF, which is made of, for example, resin or the like, is provided on the rear side of the main body 1. As shown in FIGS. 4, 6(*b*) and 6(*c*), a tact switch 71 is arranged adjacently to this button 70 on a side close to the supporting part 20 (a left side in FIG. 4). A wiring plate 79 is provided so as to face the tact switch 71. By pressing the button 70 while it is OFF, the tact switch 71 descends (moved to the left side in FIG. 4) and comes in contact with the wiring plate 79, whereby electricity starts being supplied from a battery B to the driving part 30. Adversely, by pressing the button 70 while it is ON, the tact switch 71 ascends (moved to a right side in FIG. 4), whereby electricity from the battery B to the driving part 30 is shut off. The structure is not limited to the above-described aspect, and may adopt an aspect in which, while pressing the button 70, the tact switch 71 is kept lower and in contact with the wiring plate 79 so as to be in the ON state, and on the other hand, when releasing the button 70, the tact switch 71 ascends, whereby the tact switch 71 comes away from the wiring plate 79 so as to turn into the OFF state. On a circumference of the tact switch 71, a guiding part 73 which guides the tact switch 71 to the wiring plate 79 and has an opening at its center is provided. By this guiding part 73, the tact switch 71 can be moved linearly toward the wiring plate 79.

As shown in FIG. 6, a button frame 74 is provided on a circumference of the button 70. As shown in FIGS. 6(*b*), 6(*d*) and 6(*e*), the button 70 has a notch 70*a* in which a projecting part 74*a* of the button frame 74 is to be inserted. After the notch 70*a* of the button 70 is inserted into the projecting part 74*a* of the button frame 74 so as to be integrated therein, the button 70 and the button frame 74 are to be attached to the main body 1.

Figure 3:
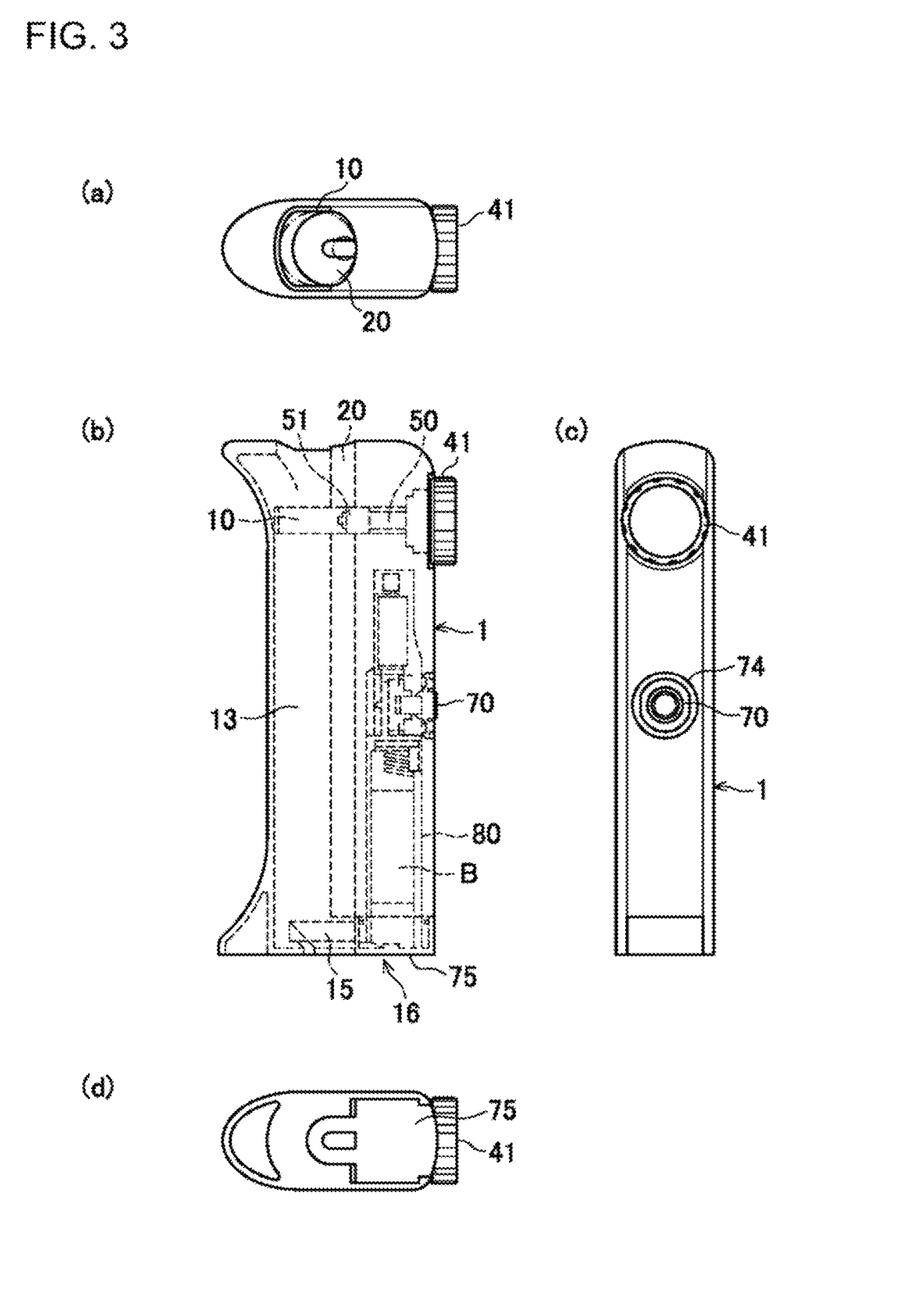
FIG. 3(a) is a plan view of the oral cleaning device according to the embodiment of the present invention.
FIG. 3(b) is a side view of the oral cleaning device, in which an internal structure is partly illustrated.
FIG. 3(c) is a rear view of the oral cleaning device.
FIG. 3(d) is a bottom view of the oral cleaning device.

As shown in FIGS. 3(*b*) and 3(*d*), a battery lid 75 which is opened and closed for the battery B to be put into and taken out from the main body 1 is provided at a lower end of the main body 1 so that the battery lid 75 can be swung. Then, between a surface of the battery lid 75 on its rear side (the right side in FIG. 4) and the main body 1, an O ring 76 is provided for preventing liquid such as water from entering a battery box 80 which stores the battery B.

In the oral cleaning device, a live part, which is not illustrated in the figures, for charging the battery B in the battery box 80 may be provided. If adopting this aspect, the battery B in the battery box 80 is to be charged with electricity supplied from the live part.

<<Effect>>

Next, explanation on effects, which can be achieved by the present embodiment having the above-described structure but are not described yet, or particularly important effects will be provided.

Figure 8:
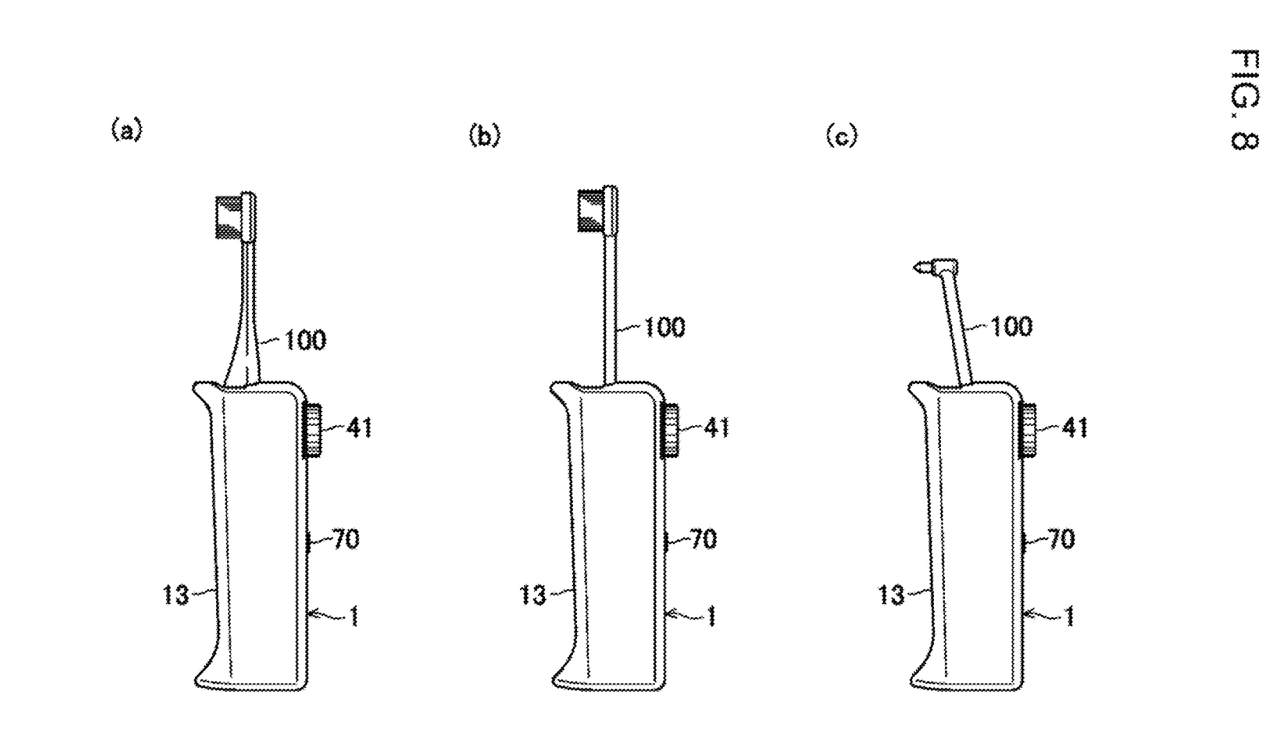
FIGS. 8(a) and 8(b) are views illustrating the oral cleaning device according to the embodiment of the present invention, to which a toothbrush as an example of an oral cleaning tool is attached.
FIG. 8(c) is a view illustrating the oral cleaning device to which an interdental brush as an example of the oral cleaning tool is attached.

According to the embodiment, the oral cleaning tool 100 can be fixed to the supporting part 20 by moving the pressing part 10 of the clamping fixing part 5 close to the supporting part 20, and the supporting part 20 and the clamping fixing part 5 are vibrated in this state, whereby the oral cleaning tool 100 fixed to the supporting part 20 can be vibrated (see FIGS. 7 and 8). Thus, only by attaching the oral cleaning tool 100 such as a commercially available tooth brush, tongue brush or interdental brush to the oral cleaning device, the oral cleaning tool 100 can be vibrated and exert a high cleaning function. As an example of such a tooth brush, a favorite tooth brush of the user is attached can work as a so-called electric tooth brush. Further, in some cases, by using a cheap tooth brush, a cleaning effect similar to that of an electric tooth brush can be obtained at a low running cost.

In the present embodiment, the pressing part 10 of the clamping fixing part 5 is movable close to or away from the supporting part 20 (see FIGS. 7(*a*) and 7(*b*)), and the oral cleaning tool 100 such as a tooth brush, a tongue brush or an interdental brush can be fixed to the supporting part 20 by moving the pressing part 10 close to the supporting part 20. Thus, the oral cleaning tool 100 having a gripping part (usually, a part to be grasped with a hand of the user) in any size can be fixed firmly to the supporting part 20. In particular, tooth brushes, tongue brushes or interdental brushes have gripping parts in generally different thicknesses, but the present embodiment is advantageous in the point that such toothbrushes, tongue brushes and interdental brushes in any thicknesses can be adopted. In addition, FIG. 8(*a*) is a view illustrating a case of attaching a tooth brush having a thick gripping part, FIG. 8(*b*) is a view illustrating a case of attaching a tooth brush having a thin gripping part, and FIG. 8(*c*) is a view illustrating a case of attaching an interdental brush. As described above, in the present embodiment, the oral cleaning tool 100 having the gripping part in any thickness can be fixed firmly.

Further, since the oral cleaning tool 100 such as a tooth brush, a tongue brush or an interdental brush can be fixed to the supporting part 20 by moving the pressing part 10 close to the supporting part 20 as described above, a play between the oral cleaning tool 100 and the supporting part 20 can be suppressed to be formed as far as possible, so that the vibrating parts 30 and 31 can vibrate the oral cleaning tool 100 efficiently.

Moreover, as shown in FIGS. 3(b) and 4, not only the clamping fixing part 5 but also the auxiliary fixing part 15 is provided, and the oral cleaning tool 100 can be fixed to the supporting part 20 at two points or more in the present embodiment. Thereby, the oral cleaning tool 100 can be fixed to the supporting part 20 more firmly, so that the vibrating parts 30 and 31 can vibrate the oral cleaning tool 100 more efficiently.

Particularly in the present embodiment, the auxiliary fixing part 15 fixes a lower end position of the oral cleaning tool 100 to the supporting part 20, and the clamping fixing part 5 fixes the oral cleaning tool 100 to the supporting part 20 at a position near the upper end of the supporting part 20. Thus, the oral cleaning tool 100 can be fixed to the supporting part 20 in good balance. Incidentally, the position near the upper end of the supporting part 20 means a region at a distance of 20% or less of a total length of the supporting part 20 in a longitudinal direction from the upper end of the supporting part 20.

In the present embodiment, only by rotating the rotating part 40 which is provided on the side surface of the supporting part 20, the pressing part 10 can be moved close to or away from the supporting part 20. By providing the rotating part 40 on the side surface (the rear side) of the supporting part 20 as described above, the rotating part 40 can be positioned where a thumb of the user is not positioned (on an opposite side of the front), whereby the user can grasp the oral cleaning device easily. Further, in the present embodiment, since the rotating part 40 is provided on the side surface of the supporting part 20, liquid such as water including toothpaste can be suppressed from entering the rotating part 40. Thereby, deterioration of the rotating part 40 can be prevented, and generation of germs in the rotating part 40 can be prevented as much as possible.

As shown in FIGS. 1(a), 1(b) and 4, in the present embodiment, the first sealing part 61 which shuts off a flow of liquid from the main body 1 into the rotating part 40 is provided. Thus, liquid such as water including toothpaste can be prevented from entering the rotating part 40 from the main body 1. Thereby, deterioration of the rotating part 40 can be prevented more securely, and generation of germs in the rotating part 40 can be prevented as far as possible.

In the present embodiment, as shown in FIG. 2, the watertight ring that composes the first sealing part 61 is provided with a pair of cuts 61a, and the wire 50 is to be inserted into these cuts 61a. Thus, the connecting mechanism composed of the wire 50 can convert the rotational motion of the rotating part 40 into linear motion and transmit the linear motion to the pressing part 10, and further can prevent liquid from entering the rotating part 40.

As shown in FIGS. 1 and 4, in the present embodiment, the rotating part 40 has the second sealing part 65 to 67 which shuts off a flow of liquid from the opposite side of the supporting part 20 (an opposite side of the main body 1 in the present embodiment) into the rotating part 40. Thus, liquid such as water including toothpaste can be prevented from entering the rotating part 40 from the opposite side of the supporting part 20. Thereby, deterioration of the rotating part 40 can be prevented more securely, and generation of germs in the rotating part 40 can be prevented as far as possible.

In the present embodiment, since the second sealing part 65 to 67 includes the O ring 65, the waterproof double-sided seal 66 and the waterproof seal 67, entering of liquid from a front surface of the rotating part 40 (the rear surface of the main body 1) can be prevented by the double-sided seal 66 and the waterproof seal 67, and entering of liquid from an inner peripheral surface of the dial 41 can be prevented by the O ring 65.

In the present embodiment, the casing 13 which covers the oral cleaning tool 100 in the height region from the lower position of the supporting part 20 to the upper position of the supporting part 20 is provided. Thus, liquid such as water including toothpaste can be suppressed from entering the rotating part 40 from the side of the supporting part 20. Particularly in the present embodiment, the casing 13 is extended from the lower end position of the supporting part 20 to an upper end position of the supporting part 20. Thereby, liquid such as water including toothpaste can be suppressed from entering the rotating part 40 from the side of the supporting part 20 more securely.

The casing 13 of the present embodiment is detachable to the main body 1. Since the casing 13 can be detached from the main body 1, the main body 1 including the casing 13 and the supporting part 20 can be washed. Thus, these casing 13 and main body 1 (supporting part 20) can be kept clean.

Further, in the present embodiment, since the lower attaching part 16 including the auxiliary fixing part 15 is detachable to the main body 1 (see FIG. 1(a)), the lower attaching part 16 including the auxiliary fixing part 15 can be detached from the main body 1 so as to be washed. Thus, the lower attaching part 16 (in particular, the auxiliary fixing part 15) can be kept clean.

Moreover, in the present embodiment, the pair of the groove parts 21 which guide the casing 13 are provided on the side surface of the main body 1, and the groove part 17 which guides the casing 13 is provided also on the lower attaching part 16. Thus, just by sliding the casing 13 along these groove part 17 and groove parts 21, the casing 13 can be detached from or attached to the main body 1. More specifically, by connecting the main body 1 with the lower attaching part 16 and subsequently moving the casing 13 upward along the groove parts 21 of the main body 1 and the groove part 17 of the lower attaching part 16, the casing 13 can be attached to the main body 1 and the lower attaching part 16. Adversely, just by moving the casing 13 downward along the groove parts 21 of the main body 1 and the groove part 17 of the lower attaching part 16, the casing 13 can be detached from the main body 1 and the lower attaching part 16. Thus, since the casing 13 can be attached to and detached from the main body 1 and the lower attaching part 16 easily, such attachment/detachment does not cause any trouble, thereby facilitating to decompose and wash the main body 1, the casing 13 and the lower attaching part 16.

Further, in the present embodiment, the casing 13 has the lower surface 13a, and this lower surface 13a is provided with the notch 13b in which the lower attaching part 16 is to be inserted. Thus, by connecting the main body 1 with the lower attaching part 16 and subsequently sliding the casing 13 upward from a lower side of the main body 1 and the lower attaching part 16 so as to attach the casing 13 to the main body 1 and the lower attaching part 16, these casing 13, main body 1 and lower attaching part 16 can be integrated. Moreover, the projecting part 18 of the lower attaching part 16 is engaged with the notch 13b, and the auxiliary fixing part 15 is provided so as to cover an upside of the projecting part 18 above this engagement, whereby liquid such as water including toothpaste can be prevented from entering between the lower attaching part 16 and the casing 13. Accordingly, a space surrounded by the main body 1, the lower attaching part 16 and the casing 13 can be prevented from being contaminated with liquid such as water including toothpaste or the like.

By the way, the above description of the embodiment and disclosure of the drawings are just an example for explaining the invention described in the claims, and the invention described in the claims is not limited by the above description of the embodiment or disclosure of the drawings.

REFERENCE SIGNS LIST

5 Clamping fixing part
10 Pressing part
13 Casing
15 Auxiliary fixing part
20 Supporting part
30 Driving part
31 Balance weight
40 Rotating part
61 First sealing part
65 O ring
66 Waterproof double-sided seal
67 Waterproof seal
100 Oral cleaning tool

What is claimed is:

1. An oral cleaning device comprising:
    a supporting part which supports an oral cleaning tool;
    a clamping fixing part which is movable close to or away from the supporting part and which fixes the oral cleaning tool to the supporting part when being moved close to the supporting part; and
    a vibrating part which vibrates the oral cleaning tool fixed to the supporting part by vibrating the supporting part or the clamping fixing part,
    wherein the supporting part is included in a main body, the oral cleaning device further comprising a rotating part which is provided on a side surface of the main body,
    wherein the clamping fixing part has a pressing part, which comes close to the supporting part and which presses the oral cleaning tool to the supporting part when the rotating part is rotated.

2. The oral cleaning device, according to claim 1, further comprising an auxiliary fixing part which fixes the oral cleaning tool to the supporting part at a lower position,
    wherein the clamping fixing part fixes the oral cleaning tool to the supporting part at an upper position compared with the auxiliary fixing part.

3. The oral cleaning device according to claim 2,
    wherein the auxiliary fixing part fixes a lower end of the oral cleaning tool to the supporting part.

4. The oral cleaning device according to claim 1,
    wherein the rotating part has a first sealing part which shuts off a flow of liquid from the main body into the rotating part.

5. The oral cleaning device according to claim 4,
    wherein the first sealing part has a watertight ring, and
    wherein the watertight ring is fitted into a depressed part which is provided on a side surface of the main body.

6. The oral cleaning device according to claim 1,
    wherein the rotating part has a second sealing part which shuts off a flow of liquid from an opposite side of the supporting part into the rotating part.

7. The oral cleaning device according to claim 6,
    wherein the rotating part has a rotating main body, which is rotatable, and a stick-on seal, which is stuck on a front surface of the rotating main body, and
    wherein the stick-on seal is included in the second sealing part.

8. The oral cleaning device according to claim 1, further comprising a casing which covers the oral cleaning tool fixed by the clamping fixing part in a height region from a lower position of the supporting part to an upper position of the supporting part.

9. The oral cleaning device, according to claim 8,
    wherein the supporting part is included in a main body, and
    wherein the casing is detachable to the main body.

10. The oral cleaning device according to claim 1, wherein the oral cleaning tool is a tooth brush, a tongue brush or an interdental brush.

* * * * *